(12) United States Patent
Hanai et al.

(10) Patent No.: US 12,306,157 B2
(45) Date of Patent: May 20, 2025

(54) METHOD FOR ANALYZING GAS AND DEVICE FOR ANALYZING GAS

(71) Applicant: PANASONIC CORPORATION, Osaka (JP)

(72) Inventors: Yosuke Hanai, Osaka (JP); Atsuo Nakao, Nara (JP); Takeshi Yanagida, Fukuoka (JP); Kazuki Nagashima, Fukuoka (JP)

(73) Assignee: PANASONIC HOLDINGS CORPORATION, Osaka (JP)

( * ) Notice: Subject to any disclaimer, the term of this patent is extended or adjusted under 35 U.S.C. 154(b) by 17 days.

(21) Appl. No.: 16/612,349

(22) PCT Filed: Apr. 20, 2018

(86) PCT No.: PCT/JP2018/016339
§ 371 (c)(1),
(2) Date: Nov. 8, 2019

(87) PCT Pub. No.: WO2018/207592
PCT Pub. Date: Nov. 15, 2018

(65) Prior Publication Data
US 2020/0096490 A1 Mar. 26, 2020

(30) Foreign Application Priority Data
May 11, 2017 (JP) ................. 2017-094759

(51) Int. Cl.
*G01N 33/00* (2006.01)
*G01N 1/22* (2006.01)
(Continued)

(52) U.S. Cl.
CPC ........... *G01N 33/0011* (2013.01); *G01N 1/22* (2013.01); *G01N 1/405* (2013.01); *G01N 2030/008* (2013.01)

(58) Field of Classification Search
CPC ......... G01N 2030/008; G01N 2030/75; G01N 33/011
See application file for complete search history.

(56) References Cited

U.S. PATENT DOCUMENTS

| 6,858,318 B2 | 2/2005 | Kogiso et al. |
| 2002/0002857 A1 | 1/2002 | Aoyama et al. |

(Continued)

FOREIGN PATENT DOCUMENTS

| CN | 1719249 A | 1/2006 |
| CN | 101657710 A | 2/2010 |

(Continued)

OTHER PUBLICATIONS

JP-2014083488-A-English (Year: 2014).*

(Continued)

*Primary Examiner* — Kristina M Deherrera
*Assistant Examiner* — Fatemeh Esfandiari Nia
(74) *Attorney, Agent, or Firm* — Rimon P.C.

(57) ABSTRACT

A method for analyzing a gas includes: allowing a sample gas to be adsorbed by each of a plurality of adsorbents (70) respectively having compositions that are different from each other; allowing the sample gas to be desorbed individually from the adsorbents (70) while detecting individually the sample gas desorbed from each of the adsorbents (70) so as to acquire desorption profiles of the sample gas that are respectively unique to the adsorbents (70); and identifying the sample gas by using a group of the desorption profiles. The acquiring of the desorption profiles is carried out by detecting, individually and over time, the sample gas desorbed from each of the adsorbents (70). Each of the desorption profiles is, for example, an overtime data created from a detection signal reflecting a quantity of the sample gas.

19 Claims, 12 Drawing Sheets

(51) Int. Cl.
G01N 1/40 (2006.01)
G01N 30/00 (2006.01)

(56) References Cited

U.S. PATENT DOCUMENTS

| | | | |
|---|---|---|---|
| 2008/0008625 A1* | 1/2008 | Thomas | G01N 1/2214 |
| | | | 422/91 |
| 2009/0275852 A1 | 11/2009 | Oki et al. | |
| 2010/0018288 A1* | 1/2010 | Yamanaka | G01N 30/76 |
| | | | 73/24.02 |
| 2012/0216597 A1* | 8/2012 | Park | G01N 1/405 |
| | | | 73/23.41 |
| 2017/0212069 A1 | 7/2017 | Nakao et al. | |
| 2018/0149565 A1 | 5/2018 | Nakao et al. | |
| 2018/0237294 A1* | 8/2018 | Giordano | B82Y 30/00 |
| 2019/0151584 A1* | 5/2019 | Kuck | A61M 16/0066 |
| 2019/0353639 A1* | 11/2019 | Bazemore | A61B 5/082 |

FOREIGN PATENT DOCUMENTS

| | | | | | |
|---|---|---|---|---|---|
| CN | 202033333 U | | 11/2011 | | |
| CN | 103018376 A | | 4/2013 | | |
| CN | 106568640 A | * | 4/2017 | | G01N 1/405 |
| JP | H11-218512 A | | 8/1999 | | |
| JP | H11-352088 A | | 12/1999 | | |
| JP | 2001-13120 A | | 1/2001 | | |
| JP | 2001013120 A | * | 1/2001 | | |
| JP | 2001-296218 A | | 10/2001 | | |
| JP | 2001305088 A | * | 10/2001 | | |
| JP | 2002-22694 A | | 1/2002 | | |
| JP | 2002035601 A | * | 2/2002 | | |
| JP | 2002-518668 A | | 6/2002 | | |
| JP | 2002-266007 A | | 9/2002 | | |
| JP | 2004-149871 A | | 5/2004 | | |
| JP | 2006-233252 A | | 9/2006 | | |
| JP | 2008-008788 A | | 1/2008 | | |
| JP | 2009-505358 A | | 2/2009 | | |
| JP | 2014083488 A | * | 5/2014 | | |
| JP | 2014228485 A | * | 12/2014 | | |
| KR | 20070027549 A | * | 3/2007 | | C01B 32/162 |
| KR | 20080101030 A | | 11/2008 | | |
| KR | 20090024515 A | * | 3/2009 | | |
| KR | 20150005361 A | * | 1/2015 | | |
| WO | 99/66304 A1 | | 12/1999 | | |
| WO | 2007/022226 A2 | | 2/2007 | | |
| WO | WO-2012035361 A1 | * | 3/2012 | | B01D 53/92 |
| WO | 2016/103561 A1 | | 6/2016 | | |
| WO | 2017/047041 A1 | | 3/2017 | | |

OTHER PUBLICATIONS

CN106568640A (Year: 2017).*
KR-20080101030-A (Year: 2008).*
Yugang Sun et al., "Large-Scale Synthesis of Uniform Silver Nanowires Through a Soft, Self-Seeding, Polyol Process," Advanced Materials, 2002, vol. 14, No. 11, pp. 833-837.
Yugang Sun et al., "Uniform Silver Nanowires Synthesis by Reducing AgNO3 with Ethylene Glycol in the Presence of Seeds and Poly(Vinyl Pyrrolidone)," Chemistry of Materials, 2002, vol. 14, No. 11, pp. 4736-4745.
Jinting Jiu et al., "Preparation of Ag nanorods with high yield by polyol process," Materials Chemistry and Physics, 2009, vol. 114, pp. 333-338.
Al Zhen, et al. "Preparation and study of a molecular sieve adsorbent for CO adsorption," Energy Chemical Industry, vol. 37 No. 6, Dec. 2016 w/English Abstract.
Search Report issued in corresponding Chinese Patent Application No. 201880030638.6, dated Sep. 6, 2021 w/ English Translation.

* cited by examiner

METHOD FOR ANALYZING GAS AND DEVICE FOR ANALYZING GAS

CROSS-REFERENCE TO RELATED APPLICATIONS

This application is the U.S. National Phase under 35 U.S.C. § 371 of International Application No. PCT/JP2018/016339, filed on Apr. 20, 2018, which claims the benefit of Japanese Application No. 2017-094759, filed on May 11, 2017, the entire contents of each are hereby incorporated by reference.

TECHNICAL FIELD

The present disclosure relates to a method for analyzing a gas and a device for analyzing a gas.

BACKGROUND ART

A method for analyzing a gas and a device for analyzing a gas can be used in various fields. For example, there is a possibility that a method for analyzing a gas and a device for analyzing a gas can diagnose people's conditions by analyzing their breath or body odor.

Patent Literature 1 describes an odor identifying device. The identifying device includes a plurality of gas sensors that have response characteristics different from each other. When a sample is measured, a signal peak is acquired from each of the gas sensors. The identifying device calculates values with regard to odor intensity and odor quality of the sample based on the signal peaks acquired.

Patent Literature 2 describes an analyzing apparatus that includes a trap and a detector. The trap has an adsorbent. Patent Literature 3 describes an apparatus that includes a sample chamber and a sensor array. The sample chamber has an adsorbent material. It is possible to detect a gas by using the apparatus of Patent Literature 2 or 3 as follows. A gas is fed into the trap or the sample chamber. The gas is adsorbed by the adsorbent of the trap or the adsorbent material of the sample chamber. The gas adsorbed by the adsorbent or the adsorbent material is desorbed. The gas desorbed from the adsorbent or the adsorbent material is fed into the detector or the sensor array to be detected by the detector or the sensor array.

CITATION LIST

Patent Literature

Patent Literature 1: JP 2001-305088 A
Patent Literature 2: JP 2001-296218 A
Patent Literature 3: JP 2002-518668 A

SUMMARY OF INVENTION

Technical Problem

There is a demand for technologies for analyzing a gas by using a simple structure.

The present disclosure is intended to provide a technology for analyzing a gas by using a simple structure.

Solution to Problem

That is, the present disclosure provides a method for analyzing a gas, including:

allowing a sample gas to be adsorbed by each of a plurality of adsorbents respectively having compositions that are different from each other;

allowing the sample gas to be desorbed individually from the adsorbents while detecting individually the sample gas desorbed from each of the adsorbents so as to acquire desorption profiles of the sample gas that are respectively unique to the adsorbents; and identifying the sample gas by using a group of the desorption profiles.

Advantageous Effects of Invention

The analyzing method of the present disclosure makes it possible to analyze the sample gas by using a simple structure.

DESCRIPTION OF EMBODIMENTS

Figure 1:
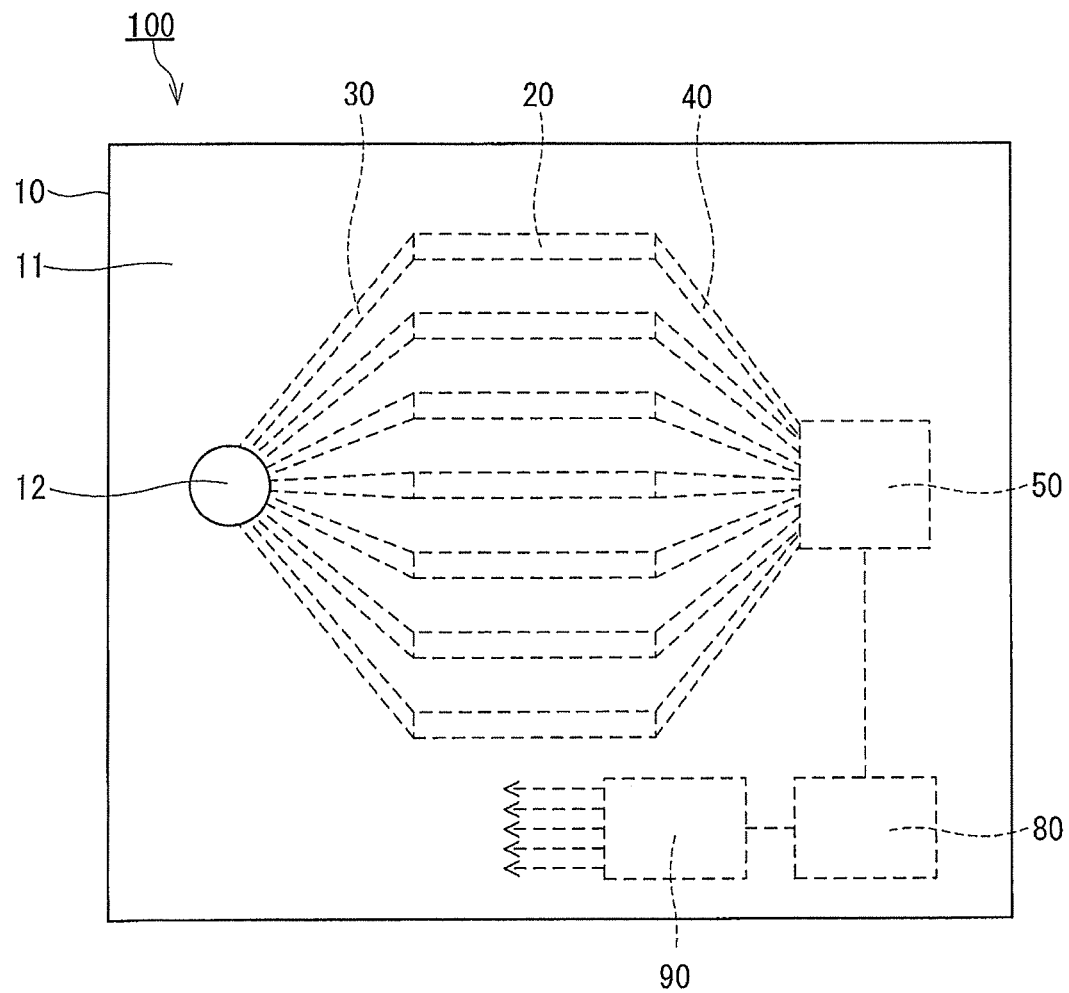
FIG. 1 is a plan view of an analyzing device according to one embodiment of the present disclosure.

A method for analyzing a gas according to a first embodiment of the present disclosure includes:

allowing a sample gas to be adsorbed by each of a plurality of adsorbents respectively having compositions that are different from each other;

allowing the sample gas to be desorbed individually from the adsorbents while detecting individually the sample gas desorbed from each of the adsorbents so as to acquire desorption profiles of the sample gas that are respectively unique to the adsorbents; and identifying the sample gas by using a group of the desorption profiles.

The first embodiment makes it possible to identify the sample gas by using the group of the desorption profiles of the sample gas that are respectively unique to the adsorbents. Therefore, highly reliable analysis results can be obtained even in the case where a small number of detectors are used. That is, it is possible to analyze the sample gas by using a simple structure.

In a second embodiment of the present disclosure according to, for example, the method for analyzing a gas according to the first embodiment, the acquiring of the desorption profiles is carried out by detecting, individually and over time, the sample gas desorbed from each of the adsorbents, and each of the desorption profiles is an overtime data created from a detection signal reflecting a quantity of the sample gas. The second embodiment makes it possible to identify the sample gas easily by using the group of the desorption profiles.

In a third embodiment of the present disclosure according to, for example, the method for analyzing a gas according to the first embodiment, the acquiring of the desorption profiles is carried out by heating each of the adsorbents so as to desorb the sample gas from the adsorbents individually, and each of the desorption profiles is a data obtained by associating a detection signal reflecting a quantity of the sample gas with a temperature change in each of the adsorbents. The third embodiment makes it possible to desorb the sample gas from each of the adsorbents easily by heating each of the adsorbents. Furthermore, the third embodiment makes it possible to identify the sample gas easily by using the group of the desorption profiles.

In a fourth embodiment of the present disclosure according to, for example, the method for analyzing a gas according to the third embodiment, the heating of each of the adsorbents is carried out with a heater. The fourth embodiment makes it possible to desorb the sample gas from each of the adsorbents easily.

In a fifth embodiment of the present disclosure according to, for example, the method for analyzing a gas according to any one of the first embodiment to the fourth embodiment, a detector that detects the sample gas desorbed from each of the adsorbents is used in common with the adsorbents. The fifth embodiment makes it possible to analyze the sample gas by using a simple structure.

In a sixth embodiment of the present disclosure according to, for example, the method for analyzing a gas according to the fifth embodiment, the adsorbents include a first adsorbent and a second adsorbent, the second adsorbent is, among the adsorbents, an adsorbent from which the sample gas is to be desorbed subsequently after being desorbed from the first adsorbent, the sample gas desorbed from the first adsorbent is fed into the detector in a first period and the sample gas desorbed from the second adsorbent is fed into the detector in a second period, and the first period and the second period are apart from each other. According to the sixth embodiment, the first period and the second period are apart from each other. Therefore, the detector can detect individually the sample gas desorbed from each of the first adsorbent and the second adsorbent. That is, the group of the desorption profiles can be acquired even in the case where one unit of detector is used. Thereby, it is possible to analyze the sample gas by using a simple structure.

In a seventh embodiment of the present disclosure according to, for example, the method for analyzing a gas according to any one of the first embodiment to the sixth embodiment, the identifying of the sample gas includes conducting a principal component analysis on the group of the desorption profiles. The seventh embodiment makes it possible to identify the sample gas easily.

In an eighth embodiment of the present disclosure according to, for example, the method for analyzing a gas according to any one of the first embodiment to the seventh embodiment, the identifying of the sample gas includes specifying a component contained in the sample gas. The eighth embodiment makes it possible to analyze the sample gas by using a simple structure.

A device for analyzing a gas according to ninth embodiment of the present disclosure includes:

a plurality of adsorbents respectively having compositions that are different from each other;

a plurality of housing parts individually storing the adsorbents;

a plurality of gas-guiding passages that guide a sample gas to be analyzed to each of the housing parts;

a detector that detects the sample gas desorbed from each of the adsorbents;

a plurality of desorbed-gas passages connecting the housing parts to the detector; and an identifier that acquires a detection signal from the detector so as to create desorption profiles of the sample gas that are respectively unique to the adsorbents, and that identifies the sample gas by using a group of the desorption profiles.

The ninth embodiment makes it possible to identify the sample gas by using the group of the desorption profiles of the sample gas that are respectively unique to the adsorbents. Therefore, highly reliable analysis results can be obtained even in the case where a small number of detectors are used. That is, it is possible to analyze the sample gas by using a simple structure.

In a tenth embodiment of the present disclosure according to, for example, the device for analyzing a gas according to the ninth embodiment, the device further includes a plurality of heaters that are respectively disposed in the housing parts and that heat the adsorbents so as to desorb the sample gas from each of the adsorbents. The heaters can be energized individually. The tenth embodiment makes it possible to desorb the sample gas from each of the adsorbents easily.

In an eleventh embodiment of the present disclosure according to, for example, the device for analyzing a gas according to the tenth embodiment, the device further includes a controller that controls electric power supply to the heaters. The adsorbents include a first adsorbent and a second adsorbent. The heaters include a first heater that heats the first adsorbent and a second heater that heats the second adsorbent. In the case where the second adsorbent is, among the adsorbents, an adsorbent from which the sample gas is to be desorbed subsequently after being desorbed from the first adsorbent, the controller controls electric power supply to the first heater and the second heater so that the sample gas is desorbed from the first adsorbent and fed into the detector in a first period and the sample gas is desorbed from the second adsorbent and fed into the detector in a second period. The first period and the second period are apart from each other. According to the eleventh embodiment, the first period and the second period are apart from each other. Therefore, the detector can detect individually the sample gas desorbed from each of the first adsorbent and the second adsorbent. That is, the group of the desorption profiles can be acquired even in the case where one unit of detector is used. Thereby, it is possible to analyze the sample gas by using a simple structure.

In a twelfth embodiment of the present disclosure according to, for example, the device for analyzing a gas according to any one of the ninth embodiment to the eleventh embodiment, each of the adsorbents contains an inorganic oxide. According to the twelfth embodiment, each of the adsorbents has stability against heat. Therefore, each of the adsorbents can be used repeatedly.

In a thirteenth embodiment of the present disclosure according to, for example, the device for analyzing a gas according to the twelfth embodiment, the inorganic oxide contains at least one selected from the group consisting of a tungsten oxide, a tantalum oxide, a titanium oxide, a tin oxide, a copper oxide, a zinc oxide and a nickel oxide. The thirteenth embodiment makes it possible to use each of the adsorbents repeatedly.

In the fourteenth embodiment of the present disclosure according to, for example, the device for analyzing a gas according to the twelfth embodiment or the thirteenth embodiment, each of the adsorbents includes a nanowire covered with an inorganic oxide film, and the inorganic oxide film is composed of the inorganic oxide. According to the fourteenth embodiment, each of the adsorbents has a large surface area. Therefore, each of the adsorbents can adsorb a sufficient quantity of the sample gas easily.

Hereinafter, the embodiments of the present disclosure are described with reference to the drawings. The present disclosure is not limited to the following embodiments.

As shown in FIG. 1, a device 100 for analyzing a gas according to one embodiment of the present disclosure includes a substrate 10 and a cover 11. Each of the substrate 10 and the cover 11 has, for example, a rectangular shape when viewed in plane. The substrate 10 has two pairs of end faces; one pair of end faces face each other, and the other pair of end faces face each other. The substrate 10 has a plurality of recessed portions formed therein. The recessed portions form, inside the analyzing device 100, passages for a sample gas. The passages for a sample gas include a plurality of housing parts 20, a plurality of gas-guiding passages 30 and a plurality of desorbed-gas passages 40. The cover 11 is combined with the substrate 10 in such a manner as to cover the recessed portions of the substrate 10. The cover 11 has an opening 12 formed therein. The sample gas is fed to the inside of the analyzing device 100 through the opening 12. The opening 12 has, for example, a circular shape when viewed in plane.

Each of the housing parts 20 has a straight line shape when viewed in plane. The housing parts 20 are arranged parallel to each other. The number of the housing parts 20 is not particularly limited. The number of the housing parts 20 may be in a range of 2 to 64, and may be in a range of 2 to 32. Only one housing part 20 may be provided depending on the sample to be analyzed.

The housing parts 20 individually store the adsorbents. The adsorbents respectively have compositions that are different from each other. When a sample gas is allowed to come into contact with each of the adsorbents, each of the adsorbents adsorbs the sample gas. By allowing the sample gas to be desorbed individually from the adsorbents while detecting individually the sample gas desorbed from each of the adsorbents, it is possible to acquire desorption profiles of the sample gas that are respectively unique to the adsorbents. Typically, the number of the types of the adsorbents is equal to the number of the housing parts 20. The adsorbents include n types of adsorbents. The letter "n" denotes an integer equal to or greater than 2. The integer "n" may be in a range of 2 to 64, and may be in a range of 2 to 32. Only one kind of the adsorbent may be used depending on the sample to be analyzed.

Each of the gas-guiding passages 30 connects the opening 12 to a gas inlet of each of the housing parts 20. The gas-guiding passages 30 are passages to guide the sample gas to be analyzed to each of the housing parts 20. Typically, the number of the gas-guiding passages 30 is equal to the number of the housing parts 20.

The analyzing device 100 further includes a detector 50. The detector 50 can detect the sample gas desorbed from each of the adsorbents. In FIG. 1, the detector 50 is disposed in the recessed portion of the substrate 10. In the present embodiment, the analyzing device 100 includes one detector 50. That is, the detector 50 is used in common with the adsorbents. However, the analyzing device 100 may include two or more detectors 50. The number of the detectors 50 may be equal to the number of the housing parts 20.

The detector 50 is not particularly limited as long as it can detect a sample gas. The detector 50 is a gas sensor, for example. Examples of the gas sensor include a semiconductor gas sensor and an infrared gas sensor. The detector 50 may be an assembly of the gas sensors. To be specific, the detector 50 may be an assembly of 16 gas sensors. Examples of the detector 50 may include a gas chromatography mass spectrometer and an infrared spectrophotometer.

Each of the desorbed-gas passages 40 connects a gas outlet of each of the housing parts 20 to a gas inlet of the detector 50. The desorbed-gas passages 40 are passages to guide the sample gas from each of the housing parts 20 to the detector 50. In the case where the analyzing device 100 includes a plurality of the detectors 50, the desorbed-gas passages 40 may connect respectively the housing parts 20 to the detectors 50. When the detector 50 is an assembly of gas sensors, the desorbed gas passages 40 may connect respectively the housing parts 20 to the gas sensors. Typically, the number of the desorbed-gas passages 40 is equal to the number of the housing parts 20.

The analyzing device 100 further includes a plurality of heaters. The heaters are respectively disposed in the housing parts 20. The heaters can heat the adsorbents respectively. When the adsorbents are heated with the heaters respectively, the sample gas is desorbed from each of the adsorbents. Each of the heaters is connected to a power supply circuit. The power supply circuit can energize the heaters individually. Thereby, the sample gas can be desorbed from the adsorbents individually.

Figure 2:
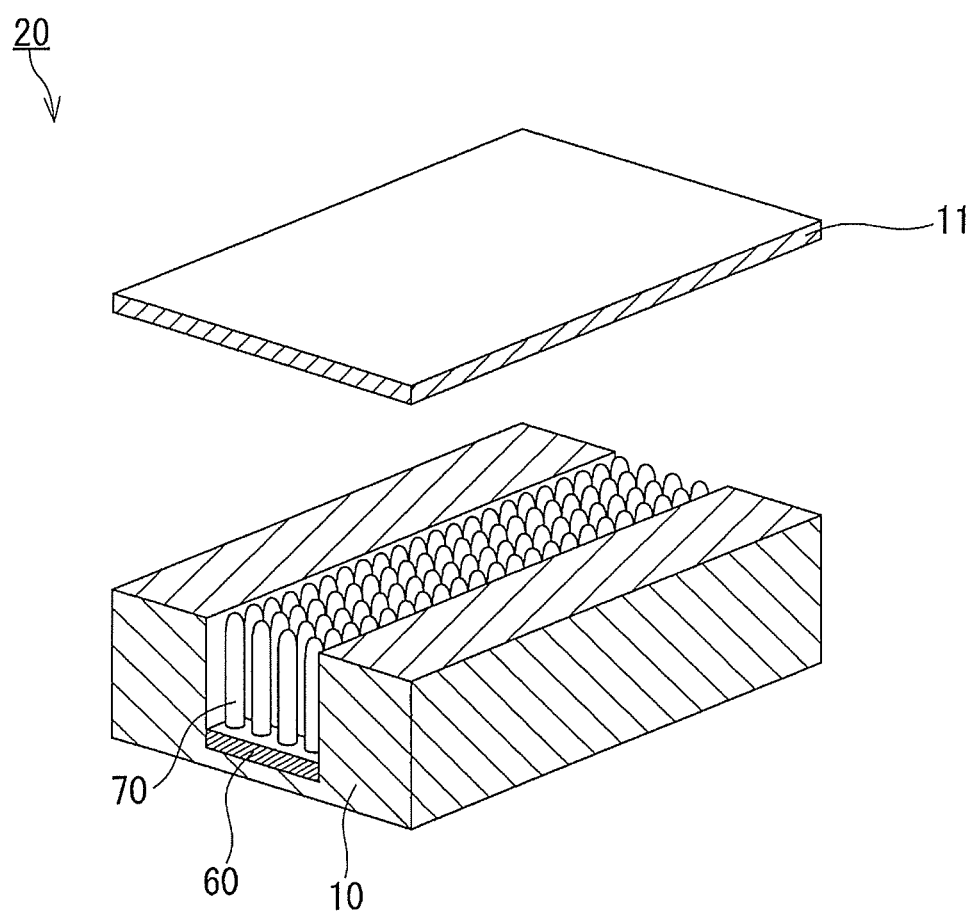
FIG. 2 is an exploded perspective view of one of a plurality of housing parts of the analyzing device shown in FIG. 1.

As shown in FIG. 2, a heater 60 is disposed on the substrate 10 that defines each of the housing parts 20. A lower surface of the heater 60 is in contact with the substrate 10. An adsorbent 70 is disposed on the heater 60. An upper surface of the heater 60 is in contact with the adsorbent 70. The heater 60 may be attached to the cover 11.

The heater 60 is a micro heater, for example. The micro heater is composed of platinum, for example. In the case where the heater 60 is the micro heater, the power consumption of the analyzing device 100 can be reduced. Examples of the heater 60 may also include an infrared heater, a resistance heating heater and an induction heating heater.

The analyzing device 100 further includes a controller 80. The controller 80 is, for example, a DSP (Digital Signal Processor) including an A/D conversion circuit, an input/output circuit, an arithmetic circuit and a memory. The controller 80 stores a program for operating the analyzing device 100 appropriately. The controller 80 controls electric power supply to a plurality of the heaters 60. Specifically, the controller 80 controls the on and off of a switch connected to each of the heaters 60. The controller 80 makes it possible to supply electric power to each of the heaters 60 individually.

The controller 80 further functions as an identifier. The controller 80 stores a program for identifying the sample gas. The detector 50 is connected to the controller 80. The controller 80 acquires a detection signal outputted from the detector 50. Based on the detection signal acquired, the controller 80 creates desorption profiles of the sample gas that are respectively unique to a plurality of the adsorbents 70. The controller 80 identifies the sample gas by using a group of the desorption profiles.

The analyzing device 100 further includes a power supply circuit 90. The power supply circuit 90 is a circuit for supplying electric power to each of the heaters 60. The power supply circuit 90 is connected to each of the heaters 60. The power supply circuit 90 includes a switch for turning on and off each of the heaters.

The analyzing device 100 further includes an input device for giving a command to the controller 80. As the input device, a mouse, a keyboard, a touchpad and a touch panel can be mentioned, for example. The analyzing device 100 further includes an output device for outputting information such as an image and an analysis result created by the controller 80. As the output device, a monitor (a display), a touch panel and a printer can be mentioned, for example.

A material of the substrate 10 and that of the cover 11 are not particularly limited. Each of the substrate 10 and the cover 11 is, for example, a silicon substrate, a metal plate, a glass plate or a high polymer film.

A material of each of the adsorbents 70 is not particularly limited as long as it can adsorb the sample gas. The material of each of the adsorbents 70 contains, for example, at least one selected from the group consisting of an inorganic oxide, an organic material and a carbon material. Typically, each of the adsorbents 70 contains the inorganic oxide. In the case where each of the adsorbents 70 contains the inorganic oxide, each of the adsorbents 70 has stability against heat. Therefore, each of the adsorbents 70 can be used repeatedly.

The inorganic oxide contains, for example, at least one selected from the group consisting of a tungsten oxide, a tantalum oxide, a titanium oxide, a tin oxide, a copper oxide, a zinc oxide, a nickel oxide, an aluminum oxide, a manganese oxide, a magnesium oxide, a silicon dioxide and a zirconium oxide. Typically, the inorganic oxide contains at least one selected from the group consisting of a tungsten oxide, a tantalum oxide, a titanium oxide, a tin oxide, a copper oxide, a zinc oxide and a nickel oxide.

The organic material contains, for example, at least one selected from the group consisting of polyalkylene glycols, polyesters, silicones, glycerols, nitriles, dicarboxylic acids and aliphatic amines. The organic material may contain at least one selected from the group consisting of polyaniline, polythiophene, polypyrrole and polyacetylene. The carbon material contains activated carbon, for example.

Each of the adsorbents 70 has a shape that is not particularly limited. Each of the adsorbents 70 has, for example, a particle shape or a fiber shape. Each of the adsorbents 70 may have a film shape. Each of the adsorbents 70 may be an inorganic oxide film composed of an inorganic oxide. As the inorganic oxide, the inorganic oxide mentioned above can be used.

Figure 3:
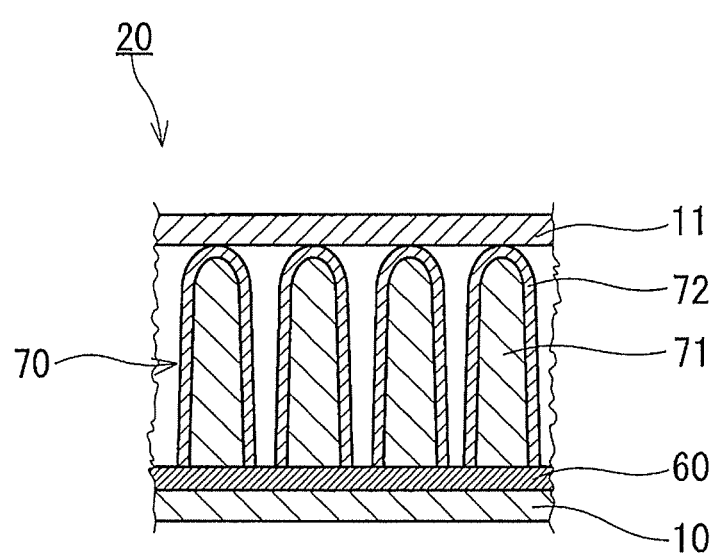
FIG. 3 is a cross-sectional view of the housing part shown in FIG. 2.

As shown in FIG. 3, each of the adsorbents 70 may include a nanowire 71 covered with an inorganic oxide film 72. FIG. 3 shows a cross section of the nanowire 71. In FIG. 3, each of the adsorbents 70 is composed of the nanowire 71 covered with the inorganic oxide film 72. The inorganic oxide film 72 is composed of the inorganic oxide. The nanowire 71 extends from the heater 60 toward the cover 11. The inorganic oxide film 72 covers the entire surface of the nanowire 71. The inorganic oxide film 72 may cover the surface of the nanowire 71 only partially. The inorganic oxide film 72 has an increased surface area by covering the nanowire 71. Thereby, the adsorbents 70 have a large surface area. Therefore, the adsorbents 70 can adsorb a sufficient quantity of the sample gas easily. In the case where the nanowire 71 is composed of a material that can adsorb the sample gas, the nanowire 71 may not be covered with the inorganic oxide film 72.

The nanowire 71 contains, for example, at least one selected from the group consisting of an inorganic oxide and a metal material. As the inorganic oxide, the inorganic oxide mentioned above can be used. The metal material contains, for example, at least one selected from the group consisting of silver, gold and copper. The material of the nanowire 71 is different from the material of the inorganic oxide film 72. Typically, the nanowire 71 contains a zinc oxide.

The nanowires 71 may have an average diameter in a range of 10 to 1000 nm. The nanowires 71 may have an average length in a range of 1 to 150 μm. The "average diameter" can be measured by the following method. A surface or cross section of the adsorbent 70 is observed with an electron microscope (a transmission electron microscope, for example). A plurality of the nanowires 71 (50 arbitrary nanowires 71, for example) observed are measured for diameter. An average calculated using the measurements obtained is determined as the average particle diameter. The "average length" can be measured by the following method. A cross section of the adsorbent 70 along a direction in which the nanowire 71 extends is observed with an electron microscope. An area of the specific nanowire 71 observed with an electron microscope is divided by a diameter of the nanowire 71 to calculate a length of the nanowire 71. Similarly, lengths of an arbitrary number (50, for example) of the nanowires 71 are calculated. An average length is determined by an average calculated using the calculated values obtained.

The fact that the nanowire 71 is covered with the inorganic oxide film 72 can be confirmed by observing the surface or cross section of the adsorbent 70 with a transmission electron microscope (TEM). The fact that the nanowire 71 is covered with the inorganic oxide film 72 can be also confirmed by conducting an elemental analysis on the surface or cross section of the adsorbent 70. The elemental analysis can be conducted by an energy dispersive X-ray analysis (EDS), for example.

A method for producing the nanowire 71 is not particularly limited. As the method for producing the nanowire 71, a liquid phase growth method and a vapor phase growth method, can be mentioned, for example. Specific methods for producing the nanowire 71 are described, for example, in JP 2009-505358 A, JP 2006-233252 A, JP 2002-266007 A, JP 2004-149871 A, Adv. Mater. 2002, 14, P 833-837, Chem. Mater. 2002, 14, P 4736-4745, or Materials Chemistry and Physics 2009, vol. 114, P 333-338. In FIG. 3, the nanowire 71 is formed on the heater 60.

A method for covering the nanowire 71 with the inorganic oxide film 72 is not particularly limited. For example, it is possible to cover the nanowire 71 with the inorganic oxide film 72 by depositing the inorganic oxide on the nanowire 71. As a method for depositing the inorganic oxide, there can be mentioned, for example, a sputtering method, an ion plating method, an electron beam evaporation method, a vacuum evaporation method, a chemical evaporation method and a chemical vapor deposition method.

In the present embodiment, the sample gas contains a volatile organic compound, for example. The volatile organic compound contains, for example, at least one selected from the group consisting of ketones, amines, alcohols, hydrocarbons, aromatic hydrocarbons, aldehydes and esters. The volatile organic compound contains, for example, at least one selected from the group consisting of propane, butane, toluene, xylene, ethanol, 2-propanol, 1-nonanol, acetone, ethyl acetate, formaldehyde, hexanal, nonanal, benzaldehyde, pyrrole and methyl chloride.

Next, a method for analyzing a gas by using the analyzing device 100 is described.

First, the sample gas is allowed to be adsorbed by each of the adsorbents respectively having compositions that are different from each other. To be specific, the analyzing device 100 is placed under an atmosphere containing the sample gas to be analyzed. The sample gas is fed to the inside of the analyzing device 100 through the opening 12 of the cover 11. The sample gas travels through each of the gas-guiding passages 30 and fed into each of the gas inlets of the respective housing parts 20. The sample gas is in contact with the adsorbents 70 in the respective housing parts 20. Thereby, each the adsorbents 70 adsorbs the sample gas.

Figure 4:
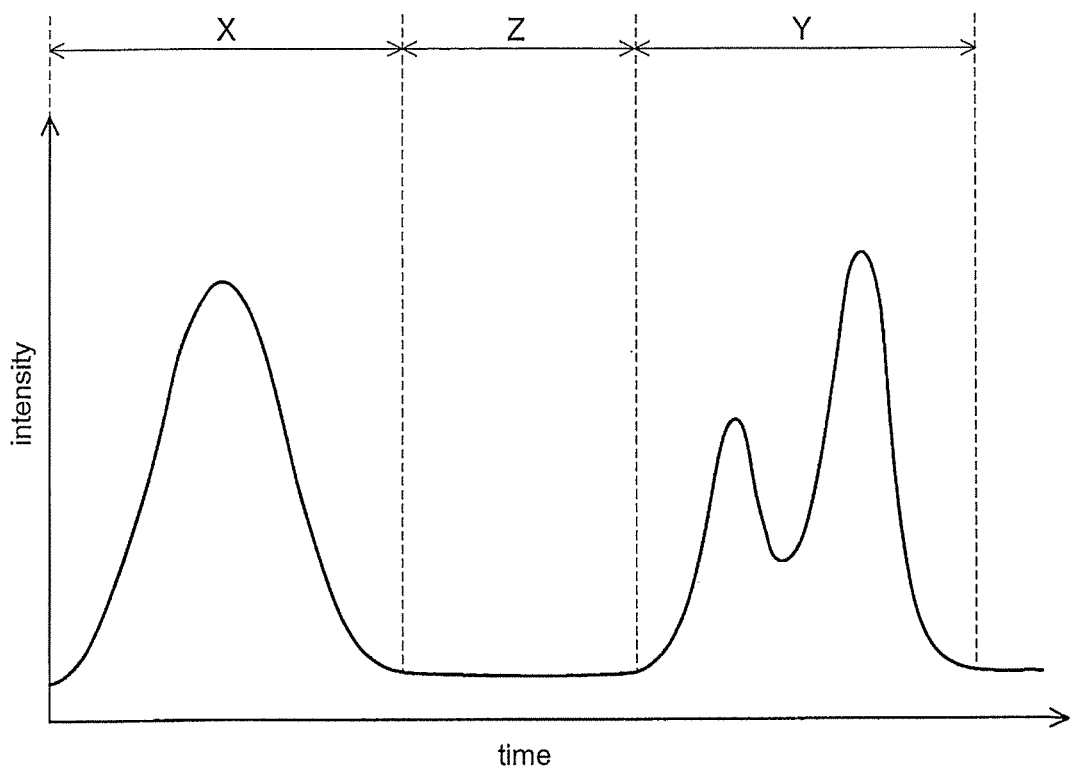
FIG. 4 is a graph for explaining a first period and a second period.

Next, the sample gas is allowed to be desorbed individually from the adsorbents 70. In the present embodiment, the adsorbents 70 include n types of adsorbents. Therefore, the sample gas is allowed to be desorbed from the n types of adsorbents in order. For example, two arbitrary adsorbents selected from the n types of adsorbents are defined as a first adsorbent and a second adsorbent. The second adsorbent is an adsorbent from which the sample gas is to be desorbed subsequently after being desorbed from the first adsorbent. As shown in FIG. 4, the sample gas desorbed from the first adsorbent is fed into the detector 50 in a first period X. The detector 50 detects over time the sample gas desorbed from the first adsorbent, for example. Thereby, a desorption profile of the sample gas unique to the first adsorbent is obtained. The horizontal axis of the graph in FIG. 4 indicates the measuring time. The vertical axis of the graph in FIG. 4 indicates the intensity of the detection signal. The sample gas desorbed from the second adsorbent in a second period Y is fed into the detector 50. The detector 50 detects over time the sample gas desorbed from the second adsorbent, for example. Thereby, the desorption profile of the sample gas unique to the second adsorbent is obtained. At this time, the first period and the second period are apart from each other (they do not overlap with each other). A preparation period Z may be present between the first period and the second period. Since the first period and the second period are apart from each other, the detector 50 can detect the sample gas desorbed from each of the first adsorbent and the second adsorbent individually. That is, two desorption profiles can be acquired by one detector 50. However, in the case where the analyzing device 100 includes a plurality of the detectors as well as the sample gas desorbed from the first adsorbent and the sample gas desorbed from the second adsorbent are detected respectively by the different detectors, the first period X may overlap with the second period Y.

A method for desorbing the sample gas is not particularly limited. The sample gas may be desorbed by heating each of the adsorbents 70. In this case, the sample gas can be desorbed from each of the adsorbents 70 easily. The adsorbents 70 can be heated respectively by the heaters 60, for example. The controller 80 controls the electric power supply to each of the heaters 60 so that the sample gas can be desorbed individually from the adsorbents 70. For example, the heater 60 to heat the first adsorbent is defined as a first heater. The heater 60 to heat the second adsorbent is defined as a second heater. The controller 80 supplies electric power to the first heater in the first period X. A temperature of the first heater rises and the first adsorbent is heated. Thereby, the sample gas is desorbed from the first adsorbent and fed into the detector 50 in the first period X. The controller 80 supplies electric power to the second heater in the second period Y. A temperature of the second heater rises and the second adsorbent is heated. Thereby, the sample gas is desorbed from the second adsorbent and fed into the detector 50 in the second period Y. The controller 80 may raise the temperature of each of the first heater and a second heater at a constant rate. In this case, the difference between the desorption profile of the sample gas unique to the first adsorbent and the desorption profile of the sample gas unique to the second adsorbent becomes clear.

The controller 80 generates the desorption profiles based on the detection signals outputted from the detector 50. The desorption profiles each are, for example, an over-time data created from a detection signal reflecting a quantity of the sample gas. The over-time data is obtained by associating the intensity of the detection signal with the measuring time. The desorption profiles each may be a data obtained by associating the intensity of the detection signal with the temperature change in each of the adsorbents 70. That is, the desorption profile may be represented in the form of a graph that shows, with its horizontal axis, the temperature change in one selected from the adsorbents 70, and that shows, with its vertical axis, the intensity of the detection signal based on the sample gas desorbed from that adsorbent. The controller 80 creates an image of the desorption profile. The controller 80 associates the adsorbent 70 with the desorption profile and records it in an internal memory thereof. In the analyzing device 100, the adsorbents 70 respectively have compositions that are different from each other. Therefore, the desorption profiles obtained from the respective adsorbents 70 are different from each other.

Next, the sample gas is identified by using a group of the desorption profiles obtained. A method for identifying the sample gas is not particularly limited. For example, it is possible to identify the sample gas by conducting data mining on the group of the desorption profiles. The data mining means an analyzing method for finding out useful information from a large volume of data, or the relevance between or among data. The data mining includes, for example, at least one selected from the group consisting of a principal component analysis and a discriminant analysis. The discriminant analysis includes, for example, at least one selected from the group consisting of a cluster analysis, machine learning, a genetic algorithm and a k-means method. The machine learning includes, for example, at least one selected from the group consisting of a neural network, a support vector machine and a self-organizing map.

The data mining makes it possible to identify the sample gas based on sameness and difference between or among the desorption profiles obtained from the respective adsorbents 70. For example, it is possible to obtain an eigenvalue by conducting the principal component analysis on the group of the desorption profiles. The eigenvalue is composed of two or three composite variables, for example. The eigenvalue falls in a specific range in accordance with sameness and difference between or among the desorption profiles. In other words, the eigenvalue falls in a specific range in accordance with the type and concentration of a component contained in the sample gas. That is, the eigenvalue falls in a specific range in accordance with the sample gas. It is possible to identify the sample gas by referring to a data obtained by associating the eigenvalue with the sample gas. The data obtained by associating the eigenvalue with the sample gas can be obtained by conducting the analyzing method of the present embodiment on the sample gas that has a known composition. The above-mentioned data may be stored in the memory of the controller 80 beforehand. The above-mentioned eigenvalue makes it possible to evaluate the sample gas in terms of, for example, odor intensity and odor quality.

By conducting the discriminant analysis on the group of the desorption profiles, it is possible to specify a component contained in the sample gas. The component contained in the sample gas can be specified by the machine learning. The discriminant analysis makes it possible also to determine whether a specific component is contained in the sample gas.

Depending on the component contained in the sample gas, it is possible, in some cases, to specify the component contained in the sample gas directly from the group of the desorption profiles without conducting the data mining. Assume that the sample gas contains a component P, for example. An interaction between the component P and the second adsorbent is stronger than an interaction between the component P and the first adsorbent. In this case, the shape of a peak defined by the desorption profile of the sample gas obtained from the first adsorbent is different significantly from the shape of a peak defined by the desorption profile of the sample gas obtained from the second adsorbent as shown in FIG. 4. To be specific, between the desorption profile obtained from the first adsorbent and that obtained from the second adsorbent, the position of the peak resulting from the component P is, in some cases, significantly different in a direction of the time axis. According to this result, it can be determined that the component P is contained in the sample gas. In FIG. 4, the desorption profile obtained from the first adsorbent is present in the first period X. The desorption profile obtained from the second adsorbent is present in the second period Y.

In the case where the analyzing device 100 includes a monitor (a display) as the output device, the monitor can display images of the desorption profiles. The monitor can also display evaluation results of the sample gas obtained by the analyzing method of the present embodiment. In the case where the analyzing device 100 includes a printer as the output device, it is possible to have the printer output the desorption profiles, etc. instead of, or in addition to having the monitor display them.

As described above, the analyzing method of the present embodiment makes it possible to obtain reliable analysis results even in the case where a small number of the detectors are used. That is, the analyzing method of the present embodiment makes it possible to analyze the sample gas by using a simple structure.

EXAMPLES

The present disclosure will be described in detail according to examples. However, the present disclosure is not limited in any way by the following examples.

(Production of Adsorbent)

First, seven flat plates were prepared. The flat plates each were a silicon wafer having an oxide film. The wafer had a diameter of 4 inches. The oxide film had a thickness of 300 Å. Nanowires composed of a zinc oxide were formed on a surface of each of the flat plates. The nanowires were produced by a hydrothermal synthesis method. To be specific, the nanowires were produced by the following method. First, 25 mmol of hexamethylenetetramine was dissolved in 1 L of ion exchanged water to prepare an aqueous solution. Next, 25 mmol of zinc nitrate hexahydrate was added to the aqueous solution obtained. Next, a polyethyleneimine aqueous solution was added to the resulting aqueous solution. The polyethyleneimine aqueous solution had a concentration of 50 wt %. The polyethyleneimine aqueous solution added contained 2.5 mmol of polyethyleneimine. The polyethyleneimine had an average molecular weight of 1800. The aqueous solution was stirred until all the reagents were dissolved so as to prepare a reaction liquid. Next, each of the flat plates was disposed in a glass vessel. At that time, a principal surface of each of the flat plates was perpendicular to a bottom of the glass vessel. Next, the reaction liquid was added in the glass vessel so that an entirety of the flat plate was in contact with the reaction liquid. The glass vessel was placed in a thermostat. The thermostat is at a temperature of 95° C. The reaction liquid was taken out from the glass vessel 12 hours after the time when the glass vessel was placed in the thermostat. Then, a new reaction liquid was added in the glass vessel, and the glass vessel was placed in the thermostat again. The exchanging of the reaction liquid in the glass vessel and the placing of the glass vessel in the thermostat were repeated until nanowires with an average length of 50 μm were formed on the principal surface of each of the flat plates. By the method just mentioned above, the nanowires were produced. The nanowires obtained had an average diameter of 400 nm. The nanowires had an average length of 50 μm.

Next, inorganic oxides respectively having compositions that are different from each other were deposited on the respective flat plates. The inorganic oxides were deposited using a high radio frequency (RF) sputtering apparatus. The inorganic oxides were deposited under the conditions that an inorganic oxide film having a thickness of 200 nm was formed on the principal surface of each of the flat plates in the case where the flat plates had no nanowires. Thereby, the nanowires were covered with the inorganic oxide film. Thus, adsorbents 1 to 7 were obtained. The adsorbent 1 included the nanowires covered with a tungsten oxide. The adsorbent 2 included the nanowires covered with a tantalum oxide. The adsorbent 3 included the nanowires covered with a titanium oxide. The adsorbent 4 included the nanowires covered with a tin oxide. The adsorbent 5 included the nanowires covered with a copper oxide. The adsorbent 6 included the nanowires covered with a zinc oxide. The adsorbent 7 included the nanowires covered with a nickel oxide.

Figure 5:
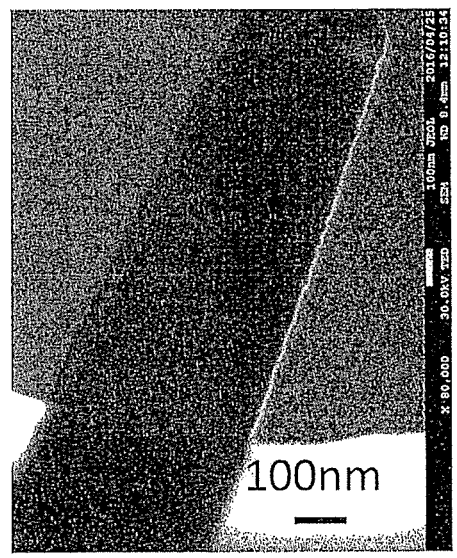
FIG. 5 is an image of an adsorbent 1 used in Measurement Examples 1 to 7 observed by a transmission electron microscope.

FIG. 5 is an image of a surface of one nanowire included in the adsorbent 1 observed by a transmission electron microscope. As shown in FIG. 5, the nanowire was covered with the inorganic oxide film (the tungsten oxide). The inorganic oxide film had a thickness of 10 nm. The inorganic oxide film covered the surface of the nanowire over a 10 μm region from a tip of the nanowire.

Measurement Example 1

2 μL of liquid pyrrole was added in a sealable vessel. Then, the adsorbent 1 was further added in the vessel. The adsorbent 1 was disposed so as not to be in direct contact with the liquid pyrrole. The vessel was sealed and left under a room temperature for 1 minute. The liquid pyrrole was partially volatilized into a gas. The adsorbent 1 adsorbed the gaseous pyrrole. The adsorbents 2 to 7 were allowed to adsorb the gaseous pyrrole in the same manner.

Next, the adsorbent 1 was placed at an inlet of a gas chromatography mass spectrometer. As the inlet, OPTIC-4 available from Shimadzu Corporation was used. A temperature in the inlet was raised from 35° C. to 300° C. at a rate of 1° C./minute. The pyrrole desorbed from the adsorbent 1 was detected over time by using the gas chromatography mass spectrometer. Thereby, a desorption profile of the pyrrole with regard to the adsorbent 1 was obtained. Desorption profiles of the pyrrole with regard to the respective adsorbents 2 to 7 were obtained in the same manner.

Figure 6:
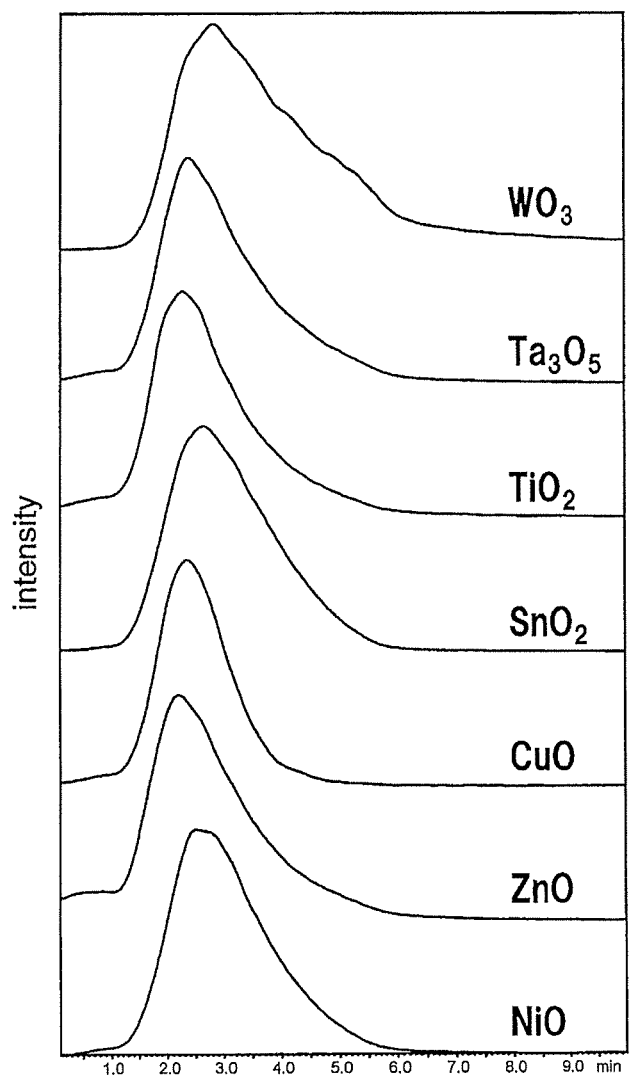
FIG. 6 is a group of desorption profiles acquired in Measurement Example 1.

The graph of FIG. 6 shows a group of the desorption profiles of the pyrrole obtained with regard to the respective adsorbents 1 to 7. The horizontal axis of the graph indicates the measuring time. The vertical axis of the graph indicates the intensity of the detection signal. The detection signal reflects the quantity of the pyrrole. In FIG. 6, the desorption profiles of the pyrrole obtained with regard to the respective adsorbents 1 to 7 were shown one above another along the vertical axis. As shown in FIG. 6, the desorption profiles were different in accordance with the compositions of the adsorbents even when the component of the sample gas remained the same. For example, the shapes of the peaks and the positions of the peaks defined by the respective desorption profiles were different in accordance with the compositions of the adsorbents.

Next, the principal component analysis was conducted on the group of the desorption profiles. First, all of the desorption profiles obtained were aligned in terms of the intensity (the vertical axis) of the detection signal. Then, the desorption profiles were arranged along the time axis (the horizontal axis) so as to obtain one data that is a succession of the desorption profiles. The principal component analysis was conducted on the data obtained. A prcomp function included in R language was used for the principal component analysis. To be specific, the data was standardized by a correlation coefficient matrix. Thereby, an eigenvalue composed of a first principal component (PC1), a second principal component (PC2) and a third principal component (PC3) was obtained.

Figure 9:
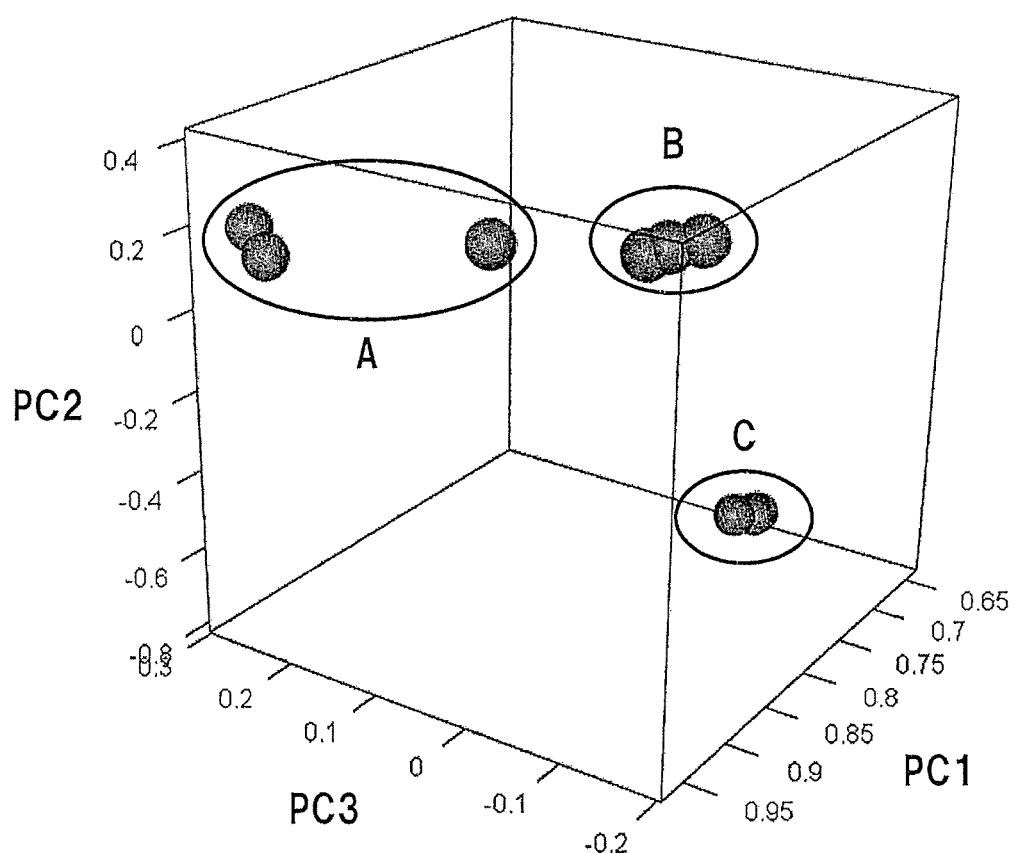
FIG. 9 is a graph showing the results of a principal component analysis conducted on each of the groups of the desorption profiles acquired in Measurement Examples 1 to 3.

Pyrrole was allowed to be adsorbed by each of the adsorbents 1 to 7 once again, and the process for obtaining the group of the desorption profiles was repeated two times. Thereby, two groups of the desorption profiles were obtained. The principal component analysis was conducted on the two groups of the desorption profiles so as to obtain two eigenvalues. As shown in FIG. 9, all of the three eigenvalues obtained in Measurement Example 1 were in a range A.

Measurement Example 2

Figure 7:
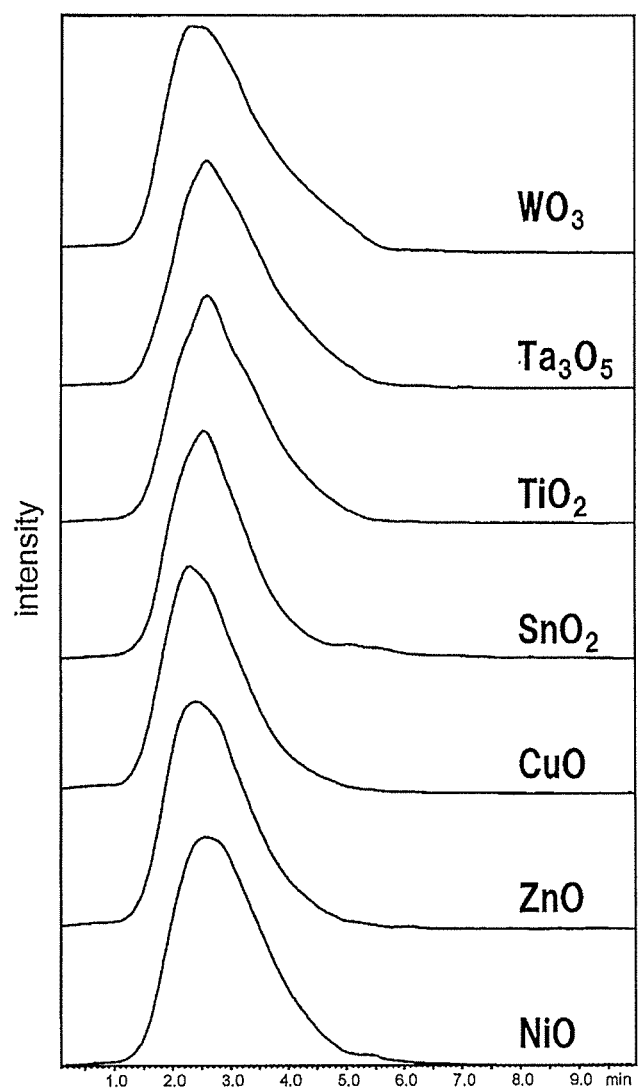
FIG. 7 is a group of desorption profiles acquired in Measurement Example 2.

Except that liquid benzaldehyde was added in the vessel instead of the pyrrole, desorption profiles of the benzaldehyde with regard to the respective adsorbents 1 to 7 were obtained in the same manner as in Measurement Example 1. The graph of FIG. 7 shows the desorption profiles of the benzaldehyde obtained with regard to the respective adsorbents 1 to 7. Next, the principal component analysis was conducted on the group of the desorption profiles so as to obtain an eigenvalue. The process for obtaining an eigenvalue with regard to the benzaldehyde was repeated two times. As shown in FIG. 9, all of the three eigenvalues obtained in Measurement Example 2 were in a range B.

Measurement Example 3

Figure 8:
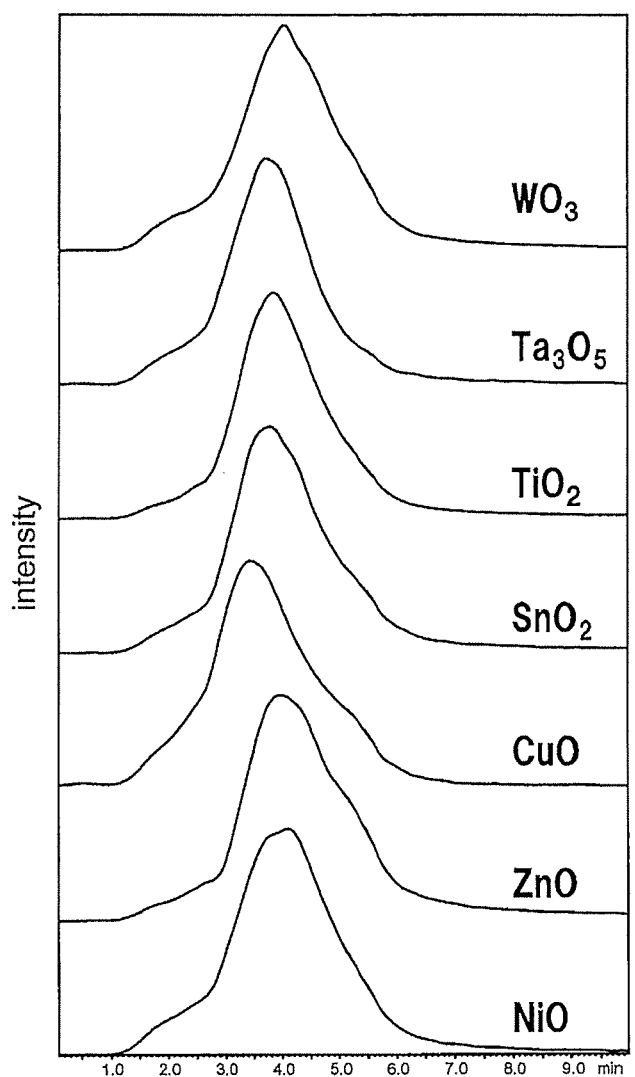
FIG. 8 is a group of desorption profiles acquired in Measurement Example 3.

Except that liquid nonanal was added in the vessel instead of the pyrrole, desorption profiles of the nonanal with regard to the respective adsorbents 1 to 7 were obtained in the same manner as in Measurement Example 1. The graph of FIG. 8 shows the desorption profiles of the nonanal obtained with regard to the respective adsorbents 1 to 7. Next, a principal component analysis was conducted on the group of the desorption profiles so as to obtain an eigenvalue. The process for obtaining the eigenvalue with regard to the nonanal was repeated two times. As shown in FIG. 9, all of the three eigenvalues obtained in Measurement Example 3 were in a range C.

As shown in FIG. 9, the ranges A to C did not overlap with each other. Therefore, according to the analyzing method of the present embodiment, it is possible to identify an unknown sample gas by using an eigenvalue thereof. For example, an eigenvalue is acquired with regard to an unknown sample gas. In the case where the unknown sample gas is pyrrole, the eigenvalue obtained is in the range A.

Measurement Example 4

Figure 10:
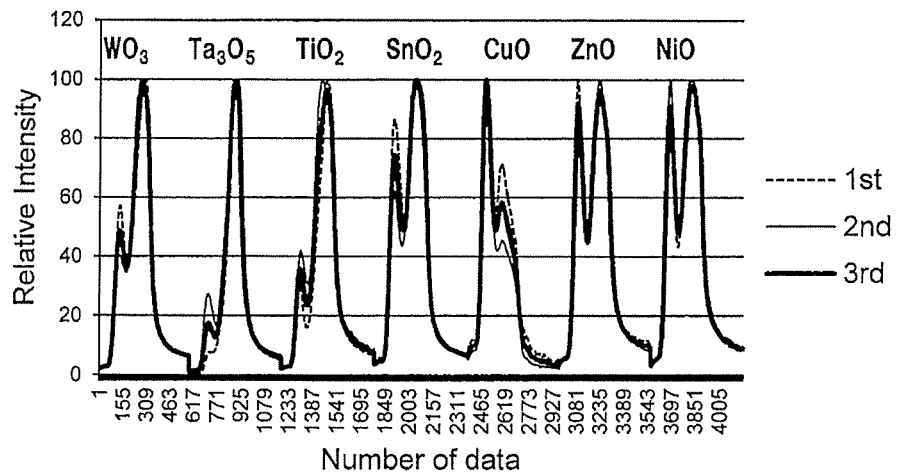
FIG. 10 is a group of desorption profiles acquired in Measurement Example 4.

Except that a mixed solution of pyrrole, benzaldehyde and nonanal was added in the vessel instead of the pyrrole, desorption profiles of the mixed composition with regard to the respective adsorbents 1 to 7 were obtained in the same manner as in Measurement Example 1. In the mixed solution, a volume ratio of pyrrole, benzaldehyde and nonanal was 1:1:1. All of the desorption profiles obtained were aligned in terms of the intensity (the vertical axis) of the detection signal. Then, the desorption profiles were arranged along the time axis (the horizontal axis) so as to obtain one data that is a succession of the desorption profiles. Next, the process for obtaining the group of the desorption profiles of the mixed composition was repeated two times. For every group of the desorption profiles obtained, one data that is a succession of the desorption profiles was obtained. FIG. 10 shows three data that overlap with each other. The horizontal axis of the graph indicates the measuring time. The vertical axis of the graph indicates the intensity of the detection signal.

Figure 14:
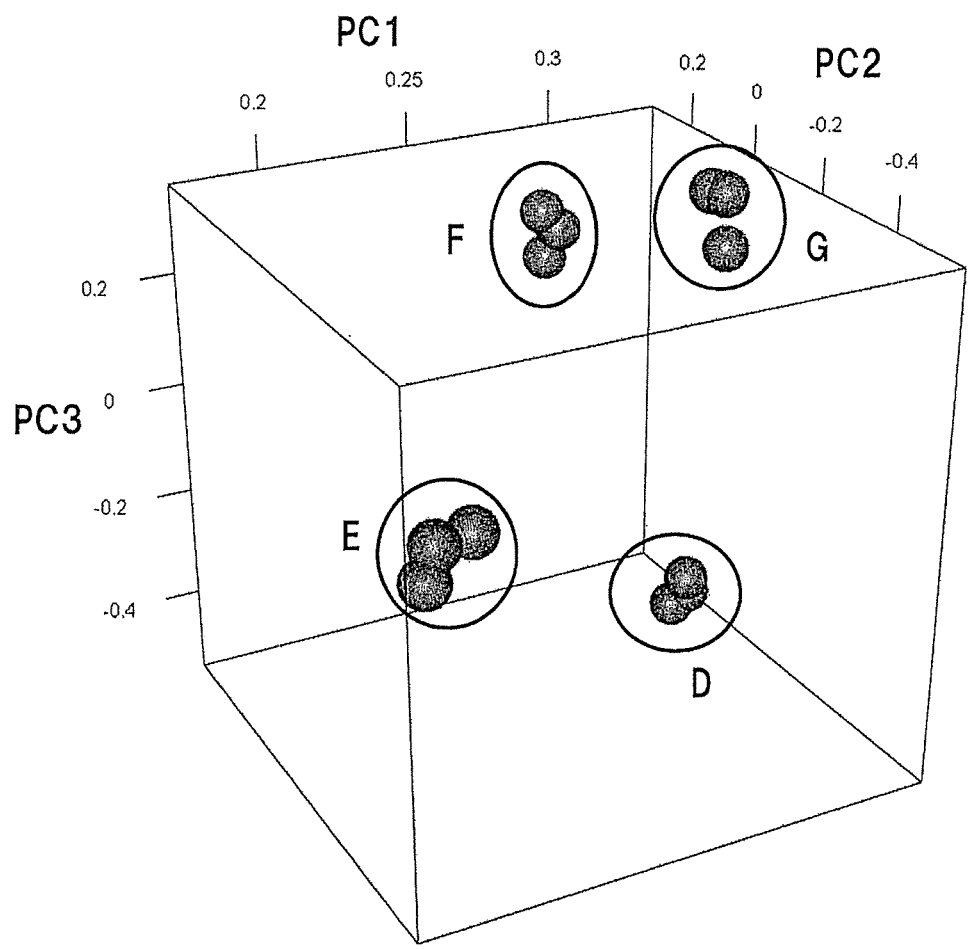
FIG. 14 is a graph showing the results of a principal component analysis conducted on each of the groups of the desorption profiles acquired in Measurement Examples 4 to 7.

The principal component analysis was conducted on the three groups of the desorption profiles so as to obtain three eigenvalues. As shown in FIG. 14, all of the three eigenvalues obtained in Measurement Example 4 were in a range D.

Measurement Example 5

Figure 11:
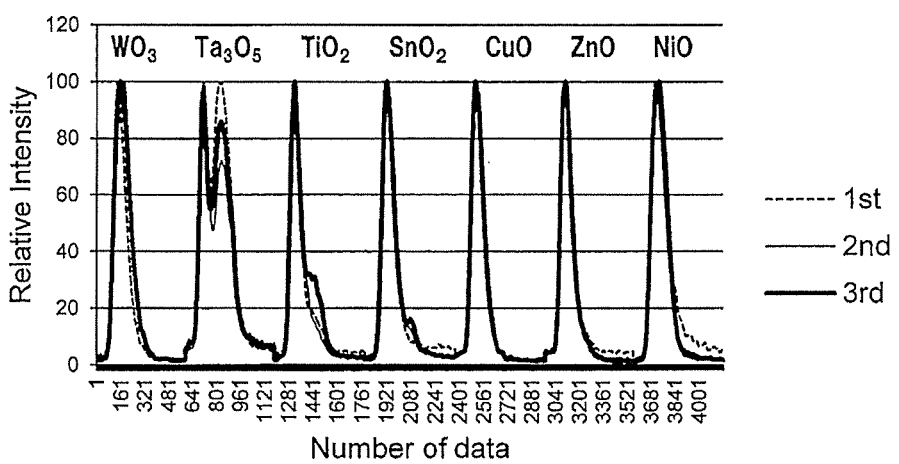
FIG. 11 is a group of desorption profiles acquired in Measurement Example 5.

Except that a mixed solution of pyrrole and benzaldehyde was added in the vessel as the mixed solution, desorption profiles of the mixed composition with regard to the respective adsorbents 1 to 7 were obtained in the same manner as in Measurement Example 4. In the mixed solution, a volume ratio of pyrrole and benzaldehyde was 1:1. All of the desorption profiles obtained were aligned in terms of the intensity (the vertical axis) of the detection signal. Then, the desorption profiles were arranged along the time axis (the horizontal axis) so as to obtain one data that is a succession of the desorption profiles. Next, the process for obtaining the group of the desorption profiles of the mixed composition was repeated two times. For every group of the desorption profiles obtained, one data that is a succession of the desorption profiles was obtained. FIG. 11 shows three data that overlap with each other. The principal component analysis was conducted on the three groups of the desorption profiles so as to obtain three eigenvalues. As shown in FIG.

14, all of the three eigenvalues obtained in Measurement Example 5 were in a range E.

Measurement Example 6

Figure 12:
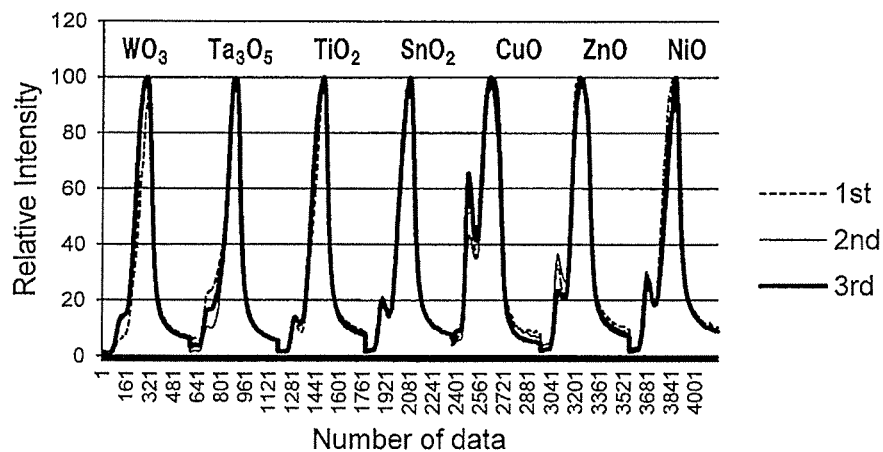
FIG. 12 is a group of desorption profiles acquired in Measurement Example 6.

Except that a mixed solution of pyrrole and nonanal was added in the vessel as the mixed solution, desorption profiles of the mixed composition with regard to the respective adsorbents 1 to 7 were obtained in the same manner as in Measurement Example 4. In the mixed solution, a volume ratio of pyrrole and nonanal was 1:1. All of the desorption profiles obtained were aligned in terms of the intensity (the vertical axis) of the detection signal. Then, the desorption profiles were arranged along the time axis (the horizontal axis) so as to obtain one data that is a succession of the desorption profiles. Next, the process for obtaining the group of the desorption profiles of the mixed composition was repeated two times. For every group of the desorption profiles obtained, one data that is a succession of the desorption profiles was obtained. FIG. 12 shows three data that overlap with each other. The principal component analysis was conducted on the three groups of the desorption profiles so as to obtain three eigenvalues. As shown in FIG. 14, all of the three eigenvalues obtained in Measurement Example 6 were in a range F.

Measurement Example 7

Figure 13:
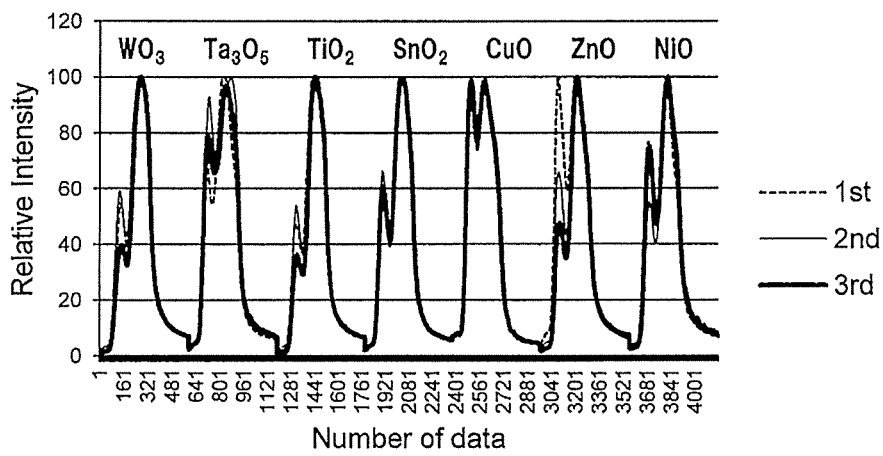
FIG. 13 is a group of desorption profiles acquired in Measurement Example 7.

Except that a mixed solution of benzaldehyde and nonanal was added in the vessel as the mixed solution, desorption profiles of the mixed composition with regard to the respective adsorbents 1 to 7 were obtained in the same manner as in Measurement Example 4. In the mixed solution, a volume ratio of benzaldehyde and nonanal was 1:1. All of the desorption profiles obtained were aligned in terms of the intensity (the vertical axis) of the detection signal. Then, the desorption profiles were arranged along the time axis (the horizontal axis) so as to obtain one data that is a succession of the desorption profiles. Next, the process for obtaining the group of the desorption profiles of the mixed composition was repeated two times. For every group of the desorption profiles obtained, one data that is a succession of the desorption profiles was obtained. FIG. 13 shows three data that overlap with each other. The principal component analysis was conducted on the three groups of the desorption profiles so as to obtain three eigenvalues. As shown in FIG. 14, all of the three eigenvalues obtained in Measurement Example 7 were in a range G.

Figure 15:
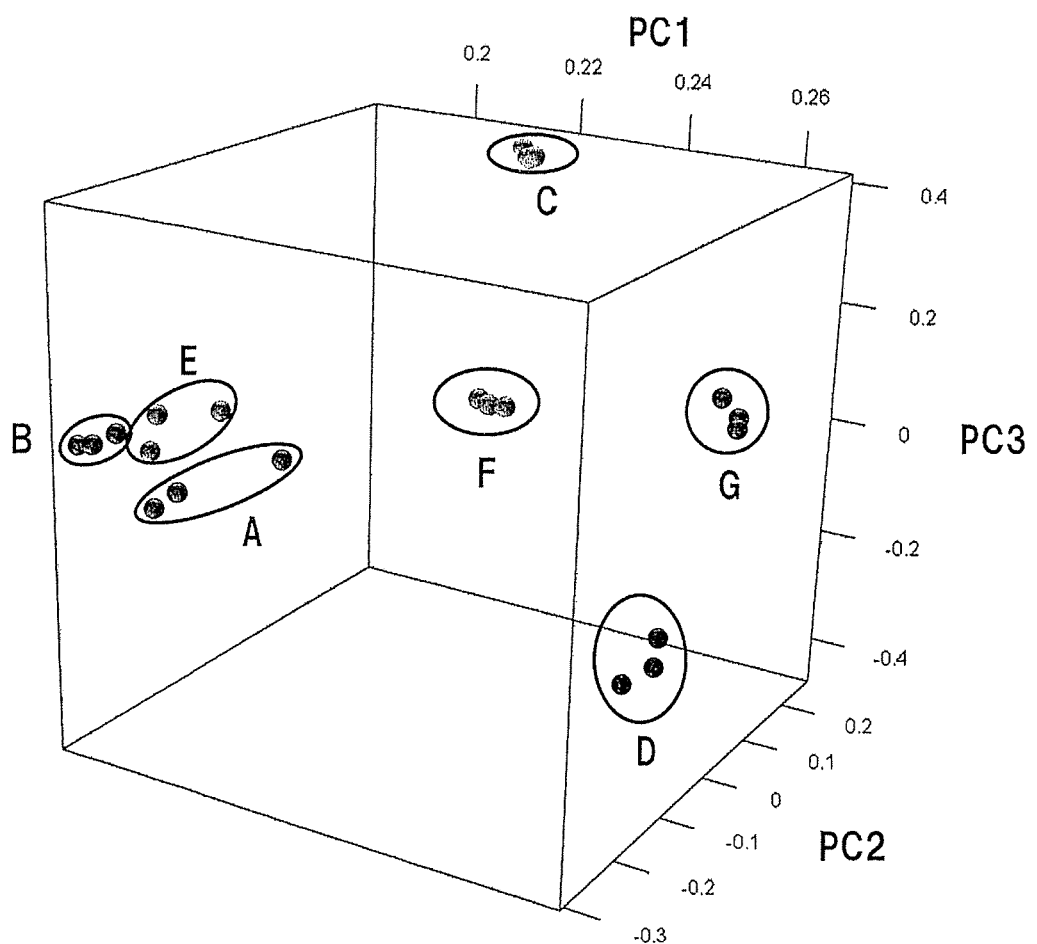
FIG. 15 is a graph showing the results of a principal component analysis conducted on each of the groups of the desorption profiles acquired in Measurement Examples 1 to 7.

As shown in FIG. 14, the ranges D to G did not overlap with each other. Furthermore, as shown in FIG. 15, the ranges A to G did not overlap with each other. Thus, according to the analyzing method of the present embodiment, it is possible to identify an unknown sample gas by using an eigenvalue thereof even in the case where the unknown sample gas contains a plurality of components.

INDUSTRIAL APPLICABILITY

The technology disclosed in the present description is useful for detection of a gas, etc.

The invention claimed is:

1. A method for analyzing a gas, comprising:
    introducing a sample gas form a gas inlet;
    allowing the sample gas to be adsorbed by each of a plurality of adsorbents at a same time, the plurality of absorbents respectively having compositions that are different from each other;
    allowing the sample gas to be desorbed individually from the plurality of adsorbents and detecting, by a detector, individually the sample gas desorbed from each of the plurality of adsorbents; and
    specifying a component contained in the sample gas based on a detection result by the detector.

2. The method for analyzing a gas according to claim 1, wherein the detector that detects the sample gas desorbed from each of the plurality of adsorbents is used in common with the plurality of adsorbents.

3. The method for analyzing a gas according to claim 2, wherein
    the plurality of adsorbents include a first adsorbent and a second adsorbent,
    the second adsorbent is, among the plurality of adsorbents, an adsorbent from which the sample gas is to be desorbed subsequently after being desorbed from the first adsorbent,
    the sample gas desorbed from the first adsorbent is fed into the detector in a first period and the sample gas desorbed from the second adsorbent is fed into the detector in a second period, and
    the first period and the second period are apart from each other.

4. The method for analyzing a gas according to claim 1, further comprising acquiring desorption profiles of the sample gas that are respectively unique to the plurality of adsorbents and respectively define peaks of which shapes and positions are different from each other.

5. The method for analyzing a gas according to claim 4, wherein the specifying the component contained in the sample gas includes conducting a machine learning on the group of the desorption profiles.

6. The method for analyzing a gas according to claim 5, wherein the acquiring of the desorption profiles is carried out by detecting, individually and over time, the sample gas desorbed from each of the plurality of adsorbents, and
    each of the desorption profiles is an over-time data created from a detection signal reflecting a quantity of the sample gas.

7. The method for analyzing a gas according to claim 5, wherein the acquiring of the desorption profiles is carried out by heating each of the plurality of adsorbents so as to desorb the sample gas from the plurality of adsorbents individually, and
    each of the desorption profiles is a data obtained by associating a detection signal reflecting a quantity of the sample gas with a temperature change in each of the plurality of adsorbents.

8. The method for analyzing a gas according to claim 7, wherein the heating of each of the plurality of adsorbents is carried out with a heater.

9. The method for analyzing a gas according to claim 1, wherein the plurality of adsorbents contain different inorganic oxide oxides, respectively.

10. The method for analyzing a gas according to claim 1, wherein:
    the plurality of absorbents are disposed in a plurality of housing parts arranged,
    the plurality of housing parts are disposed between the gas inlet and the detector, and
    the plurality of housing parts are arranged in parallel with each other between the gas inlet and the detector.

11. A device for analyzing a gas, comprising:
    a plurality of adsorbents respectively having compositions that are different from each other;

a plurality of housing parts individually storing the plurality of adsorbents, respectively;

a gas inlet for introducing a sample gas to be analyzed to each of the plurality of housing parts;

a plurality of gas-guiding passages that are connected between the gas inlet and the plurality of housing parts and guide the sample gas;

a detector that detects the sample gas desorbed from each of the plurality of adsorbents;

a plurality of desorbed-gas passages connecting the plurality of housing parts to the detector, the plurality of housing parts being disposed between the plurality of gas-guiding passages and the plurality of desorbed-gas passages; and an identifier that acquires a detection signal from the detector and specifies a component contained in the sample gas.

12. The device for analyzing a gas according to claim 11, further comprising a plurality of heaters that are respectively disposed in the plurality of housing parts and that heat the plurality of adsorbents so as to desorb the sample gas from each of the plurality of adsorbents, wherein the heaters can be energized individually.

13. The device for analyzing a gas according to claim 12, further comprising a controller that controls electric power supply to the heaters, wherein the plurality of adsorbents include a first adsorbent and a second adsorbent, the heaters include a first heater that heats the first adsorbent and a second heater that heats the second adsorbent, in the case where the second adsorbent is, among the plurality of adsorbents, an adsorbent from which the sample gas is to be desorbed subsequently after being desorbed from the first adsorbent, the controller controls electric power supply to the first heater and the second heater so that the sample gas is desorbed from the first adsorbent and fed into the detector in a first period and the sample gas is desorbed from the second adsorbent and fed into the detector in a second period, and the first period and the second period are apart from each other.

14. The device for analyzing a gas according to claim 11, wherein each of the plurality of adsorbents contains at least one selected from the group consisting of a tungsten oxide, a tantalum oxide, a titanium oxide, a tin oxide, a copper oxide, a zinc oxide and a nickel oxide.

15. The device for analyzing a gas according to claim 11, wherein each of the plurality of adsorbents includes a nanowire covered with an inorganic oxide film, and the inorganic oxide film is composed of the inorganic oxide.

16. The device for analyzing a gas according to claim 11, wherein:

the plurality of housing parts includes inlets and outlets opposite to the inlets, respectively, the plurality of gas-guiding passages are coupled to the inlets, respectively, and the plurality of desorbed-gas passages are coupled to the outlets, respectively.

17. The device for analyzing a gas according to claim 11, wherein the identifier creates desorption profiles of the sample gas that are respectively unique to the plurality of adsorbents and respectively define peaks of which shapes and positions are different from each other.

18. The device for analyzing a gas according to claim 17, wherein the identifier specifies the component contained in the sample gas by conducting a machine learning on a group of the desorption profiles.

19. The device for analyzing a gas according to claim 11, wherein the plurality of adsorbents contain different inorganic oxides, respectively.

* * * * *